(12) United States Patent
Thompson

(10) Patent No.: US 7,829,125 B1
(45) Date of Patent: Nov. 9, 2010

(54) METHOD AND PRODUCT FOR TREATING HAIR

(75) Inventor: E. Carol Thompson, Del City, OK (US)

(73) Assignee: Thompson Company, Oklahoma City, OK (US)

( * ) Notice: Subject to any disclaimer, the term of this patent is extended or adjusted under 35 U.S.C. 154(b) by 0 days.

(21) Appl. No.: 12/753,996

(22) Filed: Apr. 5, 2010

(51) Int. Cl.
*A01N 65/00* (2009.01)
(52) U.S. Cl. ...................................... 424/725
(58) Field of Classification Search ........................ None
See application file for complete search history.

(56) References Cited

U.S. PATENT DOCUMENTS 4,454,118 A * 6/1984 Johnson ....................... 424/537
6,174,533 B1 * 1/2001 SaNogueira et al. ........ 424/401

* cited by examiner

*Primary Examiner*—Michael V Meller
(74) *Attorney, Agent, or Firm*—Molly D. McKay

(57) ABSTRACT

The present invention relates to a product and method for simultaneously conditioning hair, scalp, hands and fingernails with that product. The ingredients of the product are quinine, orris root, methyl sulfonyl-methane, olive oil, coconut oil, bergamot oil, cinnamon oil, full or Virginia Island bay rum, camphor oil, and optionally panothenic acid mixed together in a petroleum jelly base. Other ingredients can also be added to the product. The product is applied by hand to treat primarily the hair and scalp to which it is applied and secondarily treats the skin and fingernails of the hands of the user when it is applied.

9 Claims, No Drawings

METHOD AND PRODUCT FOR TREATING HAIR

BACKGROUND OF THE INVENTION

1. Field of the Invention

This invention relates to a hair conditioning product and a process for producing a hair conditioner capable of increasing the strength, gloss, softness, elasticity, and thickness of hair. This invention is particularly useful on hair having undergone previous harsh treatments such as coloring or straightening. Additionally, the present invention also treats the hands and fingernails of the user as the hands are used in applying the hair condition to the hair and scalp.

2. Description of the Related Art

Hair conditioners improve the condition of hair treated with them. There are many formulas for products that condition hair. The current state of the art is inferior to the product offered in various aspects such as cost, ease of use, ingredients which may have an objectionable odor, ingredients not formulated for conditioning treated hair, and ingredients not formulated for conditioning textured hair. The present invention has the additional benefit of treating the hands and fingernails of the user as the product is applied to the hair and scalp.

SUMMARY OF THE INVENTION

This application presents a hair conditioner and a process for producing a new conditioner employing natural and artificial ingredients. The hair conditioner, made accordingly to this process, is presented to the user packaged as cream. Another form of the conditioner from this invention is as a convenient gel, paste or liquid, which is applied directly by the user who intends to shape his or her hair. Formulations of the present invention may also include, without altering the basic concepts of the present patent application: fragrances, humectants, and their functional equivalents or similar compounds, besides the other compounds used in the treatment of hair shaping and conditioning, like quaternary salts, certain dyes, relaxers, etc. In order to provide a perfect and complete idea of the invention, there will be presented some examples of formulations which can be realized to attain the objectives of this invention, that is to produce an efficient hair conditioner. However, the formulas stated here stand merely as illustrative of this invention and do not limit the invention.

DETAILED DESCRIPTION OF THE PREFERRED EMBODIMENT

The present invention is a product and method for simultaneously treating the hair, scalp, hands and fingernails of the person using the product. The product is generally made as one of two basic formulations. Although it is understood that additional ingredients may be added to the two basic formulations, the ingredients are presented below for the two basic formulations. Also, although each formulation specifies the relative proportions or parts of each ingredient, the invention is not so limited and the relative amounts of each ingredient can be increased or decrease up to approximately 50% of the amount given in the two formulations below.

Formulation No. 1

Mix together 6 parts quinine, 6 parts ground orris root, 2 parts methyl sulfonyl-methane, 8 parts olive oil, 8 parts coconut oil, 1 part bergamot oil, 1 part cinnamon oil, 1 part full bay rum or Virgin Island bay rum, and 1 part camphor oil. The mixture is added to and mixed with 48 parts softened petroleum jelly. Prior to mixing with the petroleum jelly, the petroleum jelly may be heated slightly to soften it so that it mixes easily with the other ingredients.

This formulation is then ready to be applied to the hair, which acquires gloss, softness and elasticity noticeably superior to other conditioners used by present art. The formulation is applied to the hair and scalp of the user by hand so that the formulation is simultaneously applied also to the hands and fingernails of the user, thereby also providing treatment to the hands and fingernails along with the hair and scalp.

Formulation No. 2

Mix together 6 parts quinine, 6 parts ground orris root, 2 parts methyl sulfonyl-methane, 8 parts olive oil, 8 parts coconut oil, 1 part bergamot oil, 1 part cinnamon oil, 1 part full bay rum or Virgin Island bay rum, 1 part camphor oil and 4 parts pantothenic acid. The mixture is added to and mixed with 48 parts softened petroleum jelly. Prior to mixing with the petroleum jelly, the petroleum jelly may be heated slightly to soften it so that it mixes easily with the other ingredients.

This formulation is then ready to be applied to the hair, which acquires gloss, softness and elasticity noticeably superior to other conditioners used by present art. The formulation is applied to the hair and scalp of the user by hand so that the formulation is simultaneously applied also to the hands and fingernails of the user, thereby also providing treatment to the hands and fingernails along with the hair and scalp.

While the invention has been described with a certain degree of particularity, it is manifest that many changes may be made in the details of construction and the arrangement of components without departing from the spirit and scope of this disclosure. It is understood that the invention is not limited to the embodiments set forth herein for the purposes of exemplification, but is to be limited only by the scope of the attached claim or claims, including the full range of equivalency to which each element thereof is entitled.

What is claimed is:

1. A conditioner for topical use for simultaneously treating hair and scalp of a user while also treating the hands and fingernails of the user as they apply the product wherein the product comprises:

a mixture of quinine, orris root, methyl sulfonyl-methane, olive oil, coconut oil, bergamot oil, cinnamon oil, bay rum, and camphor oil in a petroleum jelly base.

2. A conditioner according to claim 1 wherein the mixture further comprises:

pantothenic acid.

3. A conditioner according to claim 1 wherein the bay rum is selected from the group consisting of:

full bay rum and Virgin Island bay rum.

4. A conditioner according to claim 1 wherein the relative proportions of the ingredients of the conditioner further are comprise:

6 parts quinine, 6 parts ground orris root, 2 parts methyl sulfonyl-methane, 8 parts olive oil, 8 parts coconut oil, 1 part bergamot oil, 1 part cinnamon oil, 1 part bay rum, 1 part camphor oil, and 48 parts petroleum jelly.

5. A conditioner according to claim 4 wherein the mixture further comprises:

4 parts pantothenic acid.

6. A conditioner according to claim 1 wherein the relative proportions of the ingredients of the conditioner further are comprise:

between 3 and 9 parts quinine, between 3 and 9 parts ground orris root, between 1 and 3 parts methyl sulfonyl-methane, between 4 and 12 parts olive oil, between 4 and 12 parts coconut oil, between ½ and 1½ part bergamot oil, between ½ and 1½ part cinnamon oil, between ½ and 1½ part bay rum, between ½ and 1½ part camphor oil, and between 24 and 72 parts petroleum jelly.

7. A conditioner according to claim 4 wherein the mixture further comprises:

between 2 and 6 parts pantothenic acid.

8. A process for simultaneously treating the hair and scalp of a user while also treating the hands and fingernails of the user as they apply the product comprising the following steps:

mixing together quinine, orris root, methyl sulfonyl-methane, olive oil, coconut oil, bergamot oil, cinnamon oil, bay rum, and camphor oil in a petroleum jelly base to form a conditioning product, and then applying the conditioning product to the hair and scalp with the hands so that the conditioning product simultaneously treats the skin and fingernails of the hands of the user and also the hair and scalp of the head of the user.

9. A process according to claim 8 further comprising:

mixing pantothenic acid with the conditioning product before applying the conditioning product to the hair and scalp.

\* \* \* \* \*